United States Patent
Garcia et al.

(10) Patent No.: US 12,419,785 B2
(45) Date of Patent: Sep. 23, 2025

(54) PATIENT INTERFACE DEVICE FOR OPHTHALMIC SURGICAL LASER SYSTEM EMPLOYING A CAP FOR LENS CONE HANDLING

(71) Applicant: AMO DEVELOPMENT, LLC, Irvine, CA (US)

(72) Inventors: Jose Garcia, Fremont, CA (US); Christina Lagarto, Sunnyvale, CA (US); Trevor Hannon, Hayward, CA (US); Vyechi Low, San Jose, CA (US)

(73) Assignee: AMO Development, LLC, Irvine, CA (US)

( * ) Notice: Subject to any disclaimer, the term of this patent is extended or adjusted under 35 U.S.C. 154(b) by 461 days.

(21) Appl. No.: 17/662,815

(22) Filed: May 10, 2022

(65) Prior Publication Data
US 2023/0363948 A1   Nov. 16, 2023

(51) Int. Cl.
*A61F 9/009* (2006.01)
*A61B 18/20* (2006.01)
*A61F 9/008* (2006.01)

(52) U.S. Cl.
CPC .............. *A61F 9/009* (2013.01); *A61B 18/20* (2013.01); *A61F 2009/0087* (2013.01); *A61F 2009/00872* (2013.01)

(58) Field of Classification Search
CPC .............. A61F 9/009; A61F 2009/0087; A61F 2009/00872; A61B 18/20
USPC ........................................................ 606/10
See application file for complete search history.

(56) References Cited

U.S. PATENT DOCUMENTS

| | | | |
|---|---|---|---|
| 8,845,624 B2 | 9/2014 | Raksi et al. | |
| 9,849,037 B2 | 12/2017 | Rathjen et al. | |
| 10,835,421 B2* | 11/2020 | Deisinger | A61F 9/009 |
| 11,135,093 B2 | 10/2021 | Loerner et al. | |
| 2002/0103481 A1 | 8/2002 | Webb et al. | |
| 2002/0103482 A1 | 8/2002 | Scholler et al. | |
| 2013/0053837 A1* | 2/2013 | Kandulla | A61F 9/009 |
| | | | 606/4 |
| 2014/0222050 A1 | 8/2014 | Heitel et al. | |
| 2015/0190278 A1 | 7/2015 | Gooding et al. | |
| 2016/0106582 A1* | 4/2016 | Campos | A61F 9/009 |
| | | | 606/4 |

(Continued)

FOREIGN PATENT DOCUMENTS

| | | |
|---|---|---|
| FR | 3062057 A1 | 7/2018 |
| WO | 2019068866 A1 | 4/2019 |

(Continued)

*Primary Examiner* — Aaron F Roane

(57) ABSTRACT

In an ophthalmic surgical laser system, a patient interface device for coupling a patient's eye to the laser system includes a lens cone with a frustoconical shaped shell for coupling to the laser system and a suction ring for coupling to the patient's eye, the lens cone and the suction ring being joined together by clamping. A cap is provided for use with the lens cone as an installation aid. In the configuration supplied to the user, the lens cone is partially embedded in and snapped to the cap. The cap has a portion with a relatively large diameter and multiple ribs for easy handling. The user holds the cap to install the lens cone on the laser system, and pulls the cap to unsnap it from the lens cone. The lens cone is attached to the laser system with a bayonet mount that provides tactile feedback to the user.

8 Claims, 3 Drawing Sheets

(56) References Cited

U.S. PATENT DOCUMENTS

| | | | |
|---|---|---|---|
| 2016/0331586 A1 | 11/2016 | Deisinger et al. | |
| 2017/0290703 A1* | 10/2017 | Teuma | A61F 9/009 |
| 2018/0078411 A1 | 3/2018 | Fuchs et al. | |
| 2018/0177632 A1* | 6/2018 | Herekar | A61F 9/0017 |
| 2020/0253781 A1* | 8/2020 | Pössel | A61F 9/009 |
| 2020/0268553 A1 | 8/2020 | Shraiki et al. | |
| 2021/0259880 A1 | 8/2021 | Newton et al. | |
| 2021/0259881 A1* | 8/2021 | Gray | A61F 9/00745 |
| 2023/0363949 A1 | 11/2023 | Garcia et al. | |

FOREIGN PATENT DOCUMENTS

| | | | |
|---|---|---|---|
| WO | 2021170664 A1 | 9/2021 | |
| WO | 2023084482 A1 | 5/2023 | |

\* cited by examiner

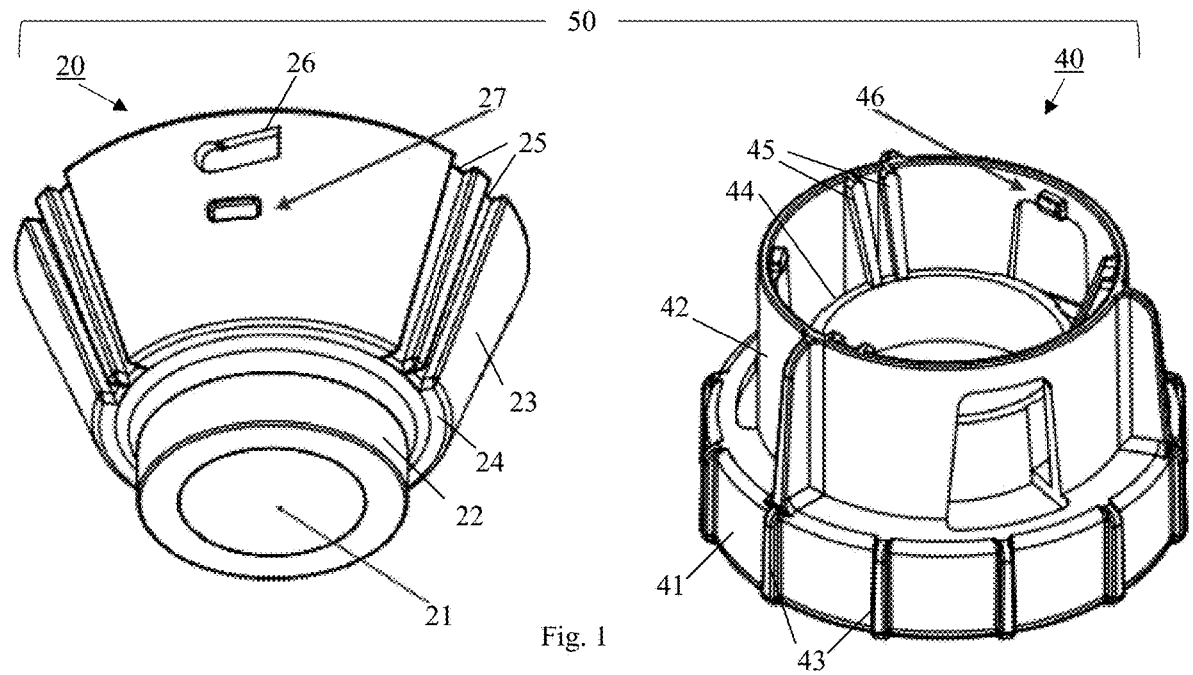
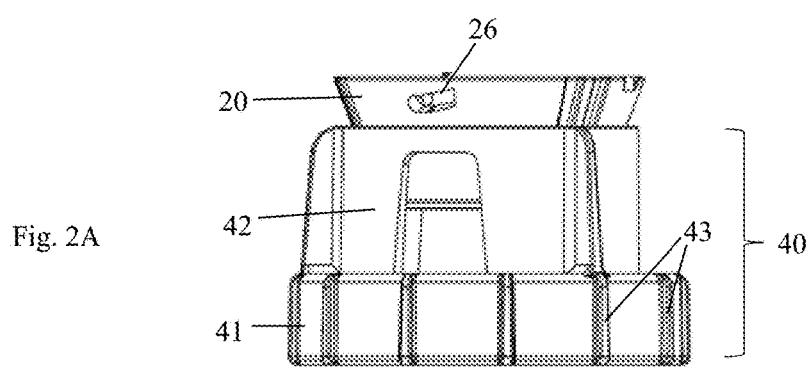
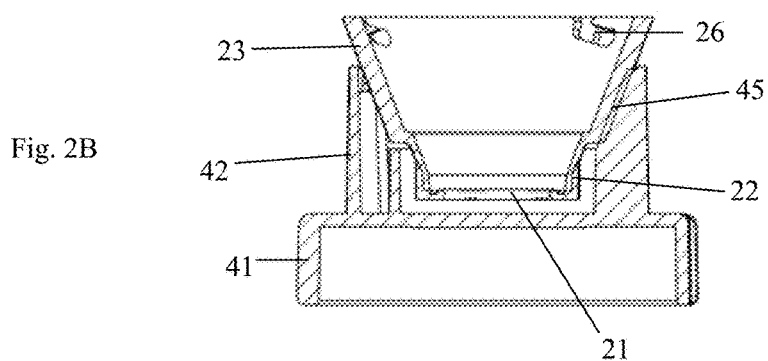
Fig. 1
Fig. 2A
Fig. 2B

PATIENT INTERFACE DEVICE FOR OPHTHALMIC SURGICAL LASER SYSTEM EMPLOYING A CAP FOR LENS CONE HANDLING

BACKGROUND OF THE INVENTION

Field of the Invention

This invention relates to ophthalmic surgical laser systems, and in particular, it relates to patient interface devices used to stabilize the patient's eye and to deliver the laser beam to the eye during ophthalmic surgery.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be treated (i.e., a portion of the patient's eye). Movement of the eye with respect to the intended focal point of the laser beam can lead to non-optimal results and might result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interfaces (PI), have been developed for coupling the patient's eye to the laser system. A PI typically has a component that directly contacts the eye, and engages and stabilizes the eye; meanwhile, the PI is attached to the laser system, so that the laser beam can be aligned to the eye. Some conventional PIs have a two-piece structure, where the component that directly contacts the eye and the component that attaches to the laser system are separate components held together by a gripping or clamping device.

For example, U.S. Pat. Appl. Pub. No. 20020103481, entitled Ocular Fixation And Stabilization Device For Ophthalmic Surgical Applications, describes a "disposable stabilization and applanation device for reconfiguring the cornea of an eye for ophthalmic laser surgery, includes an applanation lens that is disposed in a particular spatial position with respect to an incident laser beam. The applanation lens is inserted into the central opening of an attachment ring and applanates the eye in response to pressure from a lens cone. The attachment ring is coupled to the eye and includes a skirt which surrounds the applanation lens and extends outwardly therefrom to define a chamber. The skirt is formed with a groove which defines a suction channel between the attachment ring skirt and the corneal surface of an eye. A vacuum source is connected and fluid communication with the suction channel and is selectively activated to create a partial vacuum in the channel. In operation, the attachment ring is coupled to the cornea by application of suction and the applanation lens lowered into contact with the cornea through the attachment ring's central opening. A gripper structure surrounds the applanation lens and attachment ring and applies a compressive force to both components, thereby coupling the two components together. An ophthalmic surgical laser connected to the lens cone is then positioned in a well-characterized three-dimensional relationship with the applanated surface of a patient's eye." (Abstract.)

U.S. Pat. No. 10,835,421, entitled Patient Adapter For An Eye Laser Apparatus, describes a "patient adapter for an eye laser apparatus comprises a first partial adapter unit, including a suction ring portion to be placed on an eye and affixed on the eye by means of suction force, the suction ring portion having a ring axis; and a second partial adapter unit formed separately from the first partial adapter unit, the second partial adapter unit being configured for releasable coupling to the eye laser apparatus and including an eye contact element for shaping the surface of the eye, wherein the two partial adapter units are held together mechanically in a module between a first relative position, in which the eye contact element has a first axial position with respect to the suction ring portion, and a second relative position, in which the eye contact element has a second axial position with respect to the suction ring portion." (Abstract.)

U.S. Pat. Appl. Pub. No. 20130053837, entitled System and Method for Docking a Cornea with a Patient Interface Using Suction, describes a "system and method are provided for docking a patient interface device to the eye of a patient using suction. The patient interface device is formed by the structural cooperation of a base member and an attachment member, both of which have an open distal end. A contact lens is formed onto the open distal end of the base member, and a continuous abutment is formed onto the open distal end of the attachment member. When the interface device is placed onto the eye of a patient, only the continuous abutment contacts the sclera of the patient. An air pocket is formed between the contact lens and the continuous abutment. The air pocket is in fluid communication with a vacuum channel. A vacuum pump is then employed to suction the air from the air pocket and draw the surface of the eye into contact with the contact lens." (Abstract.)

U.S. Pat. No. 8,845,624, entitled Adaptive Patient Interface, describes a "patient interface for an ophthalmic system can include an attachment module, attachable to the ophthalmic system, and a contact module, configured to accommodate a viscoelastic substance between the patient interface and a procedure eye. The viscoelastic substance can include a fluid, a liquid, a gel, a cream, an artificial tear, a film, an elastic material, or a viscous material. The refractive index of the viscoelastic substance can be within a range of approximately 1.24-1.52 at an operating wavelength of the ophthalmic system. The patient interface can further include input ports, output ports, and a suction system. It can be an integrated design or a multi-piece patient interface. The viscoelastic substance can be provided by injection, on the cornea, at the contact module, or in a space bounded by soft elastic films or membranes, such as in a bag." (Abstract.)

U.S. Pat. No. 11,135,093, entitled Patient Interface For Ophthalmic Surgery, describes "a patient interface apparatus for ophthalmic surgery comprises an annular member and an evacuation conduit. The annular member has an outer side, an inner side, a distal side, and a proximal side. The inner side defines an opening that allows for a laser beam to reach a treatment region of an eye free from reflection or refraction. The proximal side has a contact surface shaped to affix to a surface of the eye, and a groove that defines a suction chamber with the surface of the eye. The evacuation conduit is capable of fluid communication with the suction chamber, and conducts fluid away from the suction chamber to affix the contact surface to the surface of the eye." (Abstract.)

SUMMARY

The present invention is directed to a patient interface device for an ophthalmic surgical laser system that substantially obviates one or more of the problems due to limitations and disadvantages of the related art.

An object of the present invention is to make it easier to handle a lens cone of the patient interface device and install it onto the laser delivery head of the laser system.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a patient interface device assembly for coupling a patient's eye to an ophthalmic surgical laser system, which includes: a lens cone configured to be coupled to the ophthalmic surgical laser system, including a frustoconical shaped shell; a suction ring, including a gripper defining a receiving opening configured to receive a portion of the lens cone, and a ring shaped flexible skirt joined to the gripper and concentric with the receiving opening, wherein the flexible skirt is configured to be coupled to the patient's eye; and a cap, having a lower portion with a cylindrical exterior shape, and a plurality of longitudinal ribs formed on an exterior surface of the lower portion and distributed along its circumference, wherein in an configuration supplied to a user, the lens cone is partially embedded inside the cap, and wherein the shell of the lens cone includes a plurality of first snap features on its exterior, and the cap includes a plurality of second snap features on its interior, wherein the first snap features and the second snap features engage with each other to attach the lens cone and the cap to each other in the supplied configuration, and wherein the first snap features and the second snap features are configured to disengage from each other in response to a separation force to separate the lens cone and the cap.

In some embodiments, the cap further includes a plurality of slanted longitudinal ribs in its interior extending inwardly from an inner wall of the cap, wherein the frustoconical shaped shell of the lens cone further includes a corresponding plurality of longitudinally extending grooves along its outer surface, and wherein in the supplied configuration, the slanted longitudinal ribs of the cap fit in the longitudinally grooves of the shell.

In some embodiments, the shell of the lens cone further includes a plurality of bayonet mount slots located near a top edge of the shell and exposed above a top edge of the cap when the lens cone and the cap are in the supplied configuration, wherein the plurality of bayonet mount slots are configured to mate with a corresponding plurality of protruding pins on the ophthalmic surgical laser system.

In another aspect, the invention provide a method of manually using the above-described patient interface device assembly to couple the patient's eye to the ophthalmic surgical laser system, including: receiving the lens cone and the cap in the delivery configuration, wherein the lens cone is partially embedded inside the cap; installing the lens cone on the ophthalmic laser system, including: holding the cap with the lens cone embedded therein, inserting the plurality of protruding pins of the ophthalmic surgical laser system into the plurality of bayonet mount slots of the lens cone, and twisting the cap to slide the bayonet mount slots relative to the pins, thereby attaching the lens cone to the ophthalmic surgical laser system; and pulling the cap to unsnap the cap from the lens cone; coupling the suction ring to the patient's eye via the flexible skirt; and joining the lens cone and the suction ring to each other by inserting the portion of the lens cone into the receiving opening of the suction ring.

In another aspect, the present invention provides a cap for use with a patient interface device for coupling a patient's eye to an ophthalmic surgical laser system, wherein the patient interface device comprises a lens cone having a frustoconical shaped shell configured to be coupled to the ophthalmic surgical laser system, and a suction ring configured to be coupled to the lens cone and to the patient's eye, the cap including: a cylindrical shaped upper portion; a cylindrical shaped lower portion, having an outer diameter larger than an outer diameter of the upper portion; and a plurality of longitudinal ribs formed on an exterior surface of the lower portion and distributed along its circumference; wherein the lens cone is partially embedded inside the cap, and wherein the shell of the lens cone includes a plurality of first snap features on its exterior, and the cap includes a plurality of second snap features on its interior, wherein the first snap features and the second snap features engage with each other to attach the lens cone and the cap to each other, and wherein the first snap features and the second snap features are configured to disengage from each other in response to a separation force to separate the lens cone and the cap.

In another aspect, the present invention provides a cap for use with a lens cone of a patient interface device for coupling a patient's eye to an ophthalmic surgical laser system, wherein the lens cone has a frustoconical shaped shell configured to be coupled to the ophthalmic surgical laser system, the cap including: a cylindrical shaped upper portion; a cylindrical shaped lower portion, having an outer diameter larger than an outer diameter of the upper portion; and a plurality of longitudinal ribs formed on an exterior surface of the lower portion and distributed along its circumference; wherein the lens cone is partially embedded inside the cap, and wherein the shell of the lens cone includes a plurality of first snap features on its exterior, and the cap includes a plurality of second snap features on its interior, wherein the first snap features and the second snap features engage with each other to attach the lens cone and the cap to each other, and wherein the first snap features and the second snap features are configured to disengage from each other in response to a separation force to separate the lens cone and the cap.

In another aspect, the present invention provides a method of manually using the above-described cap to install the lens cone on the ophthalmic surgical laser system and to couple the patient's eye to the ophthalmic surgical laser system.

It is to be understood that both the foregoing general description and the following detailed description are exemplary and explanatory and are intended to provide further explanation of the invention as claimed.

BRIEF DESCRIPTION OF THE DRAWINGS

FIG. 1 is a perspective view illustrating a lens cone and a cap according to an embodiment of the present invention, with the lens cone and cap being illustrated separately.

FIGS. 2A and 2B are a side view and a side cross-sectional view, respectively, which illustrate the lens cone and the cap snapped together according to an embodiment of the present invention.

DETAILED DESCRIPTION OF PREFERRED EMBODIMENTS

Embodiments of the present invention provide a patient interface device assembly that includes a cap that serves as an installation aid.

Figure 3:
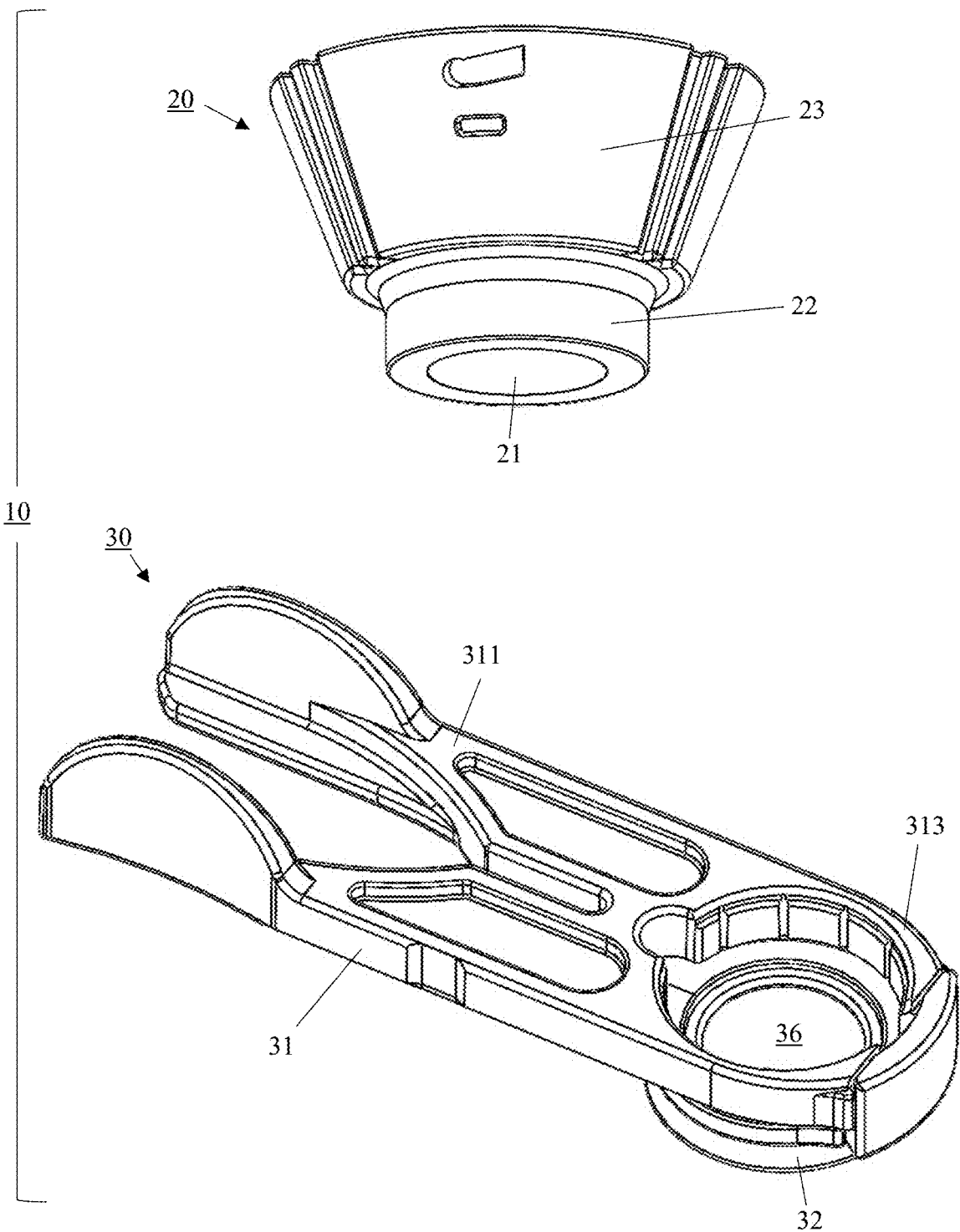
FIG. 3 is a perspective view illustrating a patient interface device which includes a lens cone and a suction ring according to an embodiment of the present invention.

As illustrated in FIG. 3, the patient interface device 10 includes two separate components, namely, a lens cone 20 having a lens 21, and a suction ring 30 which includes a gripper 31 and a ring shaped flexible skirt 32 preferably integrated as one piece. The lens cone 20 is configured to be attached to the laser delivery head of the laser system (not shown) during surgery. The suction ring 30 is configured to be coupled to the patient's eye, via the flexible skirt 32, by a vacuum force applied to a channel formed by the flexible skirt and the eye surface. The gripper 31 of the suction ring is configured to receive a cylindrical base portion 22 of the lens cone 20 in a receiving opening 36 of the suction ring, which is concentric with the flexible skirt 32, and to securely retain the lens cone by a clamping force. Preferably, the lens 21 is located near the bottom end of the base portion of the lens cone 20, and contacts the eye when the suction ring 30 is coupled to the patient's eye and the lens cone base portion 22 is inserted into and retained by the gripper 31.

The gripper 31 is constructed like a clip or clothes pin, formed by two lever handles 311 having respective jaws 313 at their distal ends. The two jaws 313 face each other to define the substantially circular shaped receiving opening 36 between them. The lever handles 311 including the jaws are formed of a hard but slightly deformable material, such as a hard plastic, for example, polycarbonate. The lever handles 311 may be squeezed toward each other to cause the two jaws 313 to open, so that the lens cone base portion 22 may be inserted into the receiving opening 36, and then relaxed to securely hold the lens cone.

The lens cone 20 is formed of a generally frustoconical shaped shell 23 made of a rigid material, for example, metal or a hard plastic such as polycarbonate, with a cylindrical base portion 22 at the smaller end of the shell. In some embodiment, a piece of soft TPE material is provided as a part of the outer surface of the base portion 22 to enable a more secure mating between the lens cone 20 and the gripper 31.

The lens cone 20 and the suction ring 30 of the patient interface are supplied to the user (surgeon) as two separate pieces. To use the patient interface to couple the patient's eye to the ophthalmic laser system, the user installs the lens cone 20 on the laser delivery head of the ophthalmic laser system, attaches the suction ring 30 to the patient's eye via the flexible skirt 32, and joins the lens cone and the suction ring to each other by inserting the lens cone base portion 22 into the receiving opening 36 of the suction ring.

Figure 4:
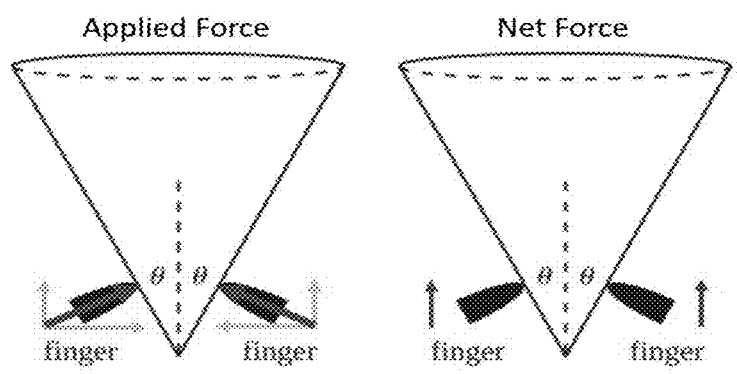
FIG. 4 is a schematic diagram that illustrates the force applied to a cone shaped component when handled by hand.

However, the lens cone 20 can be difficult to handle by hand due to its shape. Imparting a holding force on the cone shaped object causes a net vertical force upward and can cause the cone to pop out of the user's hands, as schematically illustrated in FIG. 4. The base portion 22 is small and not easy to handle. Thus, it can be difficult to install the lens cone on the laser delivery head.

To solve this and other problems, according to embodiments of the present invention, the patient interface lens cone is supplied to the user with a cylindrical cap embedding the lens cone. The cap, which has a cylindrical shaped portion with ribs surrounding its perimeter, allows the user to easily hold and install the lens cone, which is especially helpful in the use case of limited dexterity due to use while wearing gloves.

FIG. 1 (perspective view) illustrates the lens cone 20 and the cap 40 separate from each other for clarity. FIG. 2A (side view) and FIG. 2B (side cross-sectional view) illustrate the lens cone and the cap snapped together, with the lens cone partially disposed within the cap. The lower (smaller) end of the lens cone is disposed inside the cap, while the upper (larger) end of the lens cone is exposed outside of the cap, and the hollow interior of the lens cone is open at the upper end. As shown in the figures, the cap 40 has a generally cylindrical shape. In the illustrated embodiment, the lower portion (base) 41 has a larger outer diameter than the upper portion 42, and a plurality of longitudinal ribs 43 are formed on the outer surface of the base 41 and distributed along its circumference. The larger outer diameter of the base 41 and the ribs 43 facilitate easy gripping of the cap by the user's hand. As shown in FIG. 2B, the lower portion 41 is located below the lower end of the lens cone 20 as represented by the lens 21.

In some alternative embodiments, the entire cap may have the same outer diameter. In some alternative embodiments, the larger-diameter lower portion 41 may be located at a longitudinal position that overlaps with the base portion 22 of the lens cone 20 (i.e., the bottom of the lens cone is located near the bottom of the cap). The configuration illustrated in FIGS. 1, 2A and 2B, where the upper portion 42 of the cap has a smaller diameter than the lower portion 41, may have the advantage of better visibility when installing the lens cone onto the laser delivery head, as the smaller diameter of the upper portion 42 avoids unnecessarily blocking views of relevant portions of the laser delivery head.

Inside the cap 40, a circular step feature 44 is provided, and is sized to support the lens cone 20 at a corresponding circular step feature 24 located between the frustoconical shaped shell 23 and the base portion 22. The frustoconical shaped shell 23 further defines a plurality of longitudinally extending grooves 25 along its outer surface. On the inside of the cap 40, a corresponding plurality of slanted longitudinal ribs 45 are provided, extending inwardly from the inner wall, such that when the lens cone 20 is disposed inside the cap 40 and the step feature 24 of the lens cone is resting on the step feature 44 of the cap, the slanted longitudinal ribs 45 fit in the longitudinally grooves 25 of the shell 23. This configuration allows the lens cone 20 to rest inside the cap 40 and be locked at a predetermined angular position with respect to the cap, allowing the user to rotate the lens cone by rotating the cap during installation, as will be described later.

The lens cone shell 23 has a number of (e.g. three) bayonet mount features (slots) 26 that mate with a corresponding number of protruding pins on the laser delivery head. The bayonet mount slots 26 are located near the top edge of the shell 23 and exposed above the top edge of the cap 40 when the lens cone rests in the cap.

The lens cone 20 further defines a plurality of (e.g. three) snap slots 27, and the inner wall of the cap 40 has a corresponding plurality of inwardly extending snap protrusions 46. When the lens cone is situated inside the cap, the snap protrusions 46 of the cap fit in (engage) the snap slots 27 of the lens cone, forming a plurality of snaps that attach the lens cone and the cap to each other. The cap is formed of a hard but slightly deformable material, such as a hard plastic, so that the snap protrusions 46 can be pulled out of (disengaged from) the snap slots 27 to unsnap the lens cone and the cap from each other in response to a separation force.

In use, the lens cone and cap are supplied to the user as a snapped-together assembly, with the suction ring 30 supplied as a separate component. The user manually picks up and holds the cap, e.g., by the lower portion 41, and installs the lens cone onto the laser delivery head. This involves placing the lens cone against the laser delivery head so that the protruding pins on the laser delivery head are inserted into one end of the bayonet mount slots 26, and then twisting the lens cone by twisting the cap, so that the pins on the laser delivery head slide into the slightly larger end of the bayonet mount slots. Utilizing the larger diameter of the lower portion 41 of the cap 40 can provide more leverage in this process. When the lens cone is properly installed onto the laser delivery head, the user can feel the lens cone snap into place on the laser delivery head, via the bayonet mount, which confirms that the lens cone is properly installed. The user then removes the cap from the lens cone, by pulling down on the cap to unsnap the cap from the lens cone at the snap locations. In some embodiments, where the laser delivery head is a floating head, pulling down on the cap also helps to ensure that the laser delivery head is able to "bottom out" and start at the lowest position of its z-axis travel.

Subsequently, the lens cone is joined to the suction ring in a manner described earlier.

To summarize, according to embodiments of the present invention, the lens cone is provided to the user with an attached cylindrical cap that serves as an installation aid, which is removed after the lens cone is installed on the laser delivery head. This reduces the difficulties in installing the lens cone.

In this regard, it should be noted that the cap is not a part of the patient interface that will ultimately be engaged with the laser system or the patient's eye. Preferably, the cap does not include a flexible skirt at its bottom, as does the suction ring 30, nor any handles (excluding the ribs) that extend from its periphery. The cap is removably connected to the lens cone by mechanical snaps, not by a suction force.

Further, the bayonet mount between the lens cone and the laser delivery head allow the user to twist the cap on using tactile feel as the main indicator of proper attachment to the laser delivery head. This further reduces the difficulties in installation. For example, it reduces the need to bend over to find the attachment slot on the laser delivery head before sliding the lens cone in place, which is not ergonomic. It also reduces the need to use line-of-sight verification to ensure alignment.

While in the illustrated embodiment the gripper 31 and the flexible skirt 32 are integrated in one piece as the suction ring 30, in alternative embodiments, the gripper and the flexible skirt may be separate pieces, forming a three-piece patient interface device.

It will be apparent to those skilled in the art that various modification and variations can be made in the patient interface device and assembly as well as related method of use of the present invention without departing from the spirit or scope of the invention. Thus, it is intended that the present invention cover modifications and variations that come within the scope of the appended claims and their equivalents.

What is claimed is:

1. A patient interface device assembly for coupling a patient's eye to an ophthalmic surgical laser system, comprising:
    a lens cone configured to be coupled to the ophthalmic surgical laser system, including a frustoconical shaped shell;
    a suction ring, including a gripper defining a receiving opening configured to receive a portion of the lens cone, and a ring shaped flexible skirt joined to the gripper and concentric with the receiving opening, wherein the flexible skirt is configured to be coupled to the patient's eye; and
    a cap, having a lower portion with a cylindrical exterior shape, and a plurality of longitudinal ribs formed on an exterior surface of the lower portion and distributed along its circumference,
    wherein in an configuration supplied to a user, the lens cone is partially embedded inside the cap, and
    wherein the shell of the lens cone includes a plurality of first snap features on its exterior, and the cap includes a plurality of second snap features on its interior, wherein the first snap features and the second snap features engage with each other to attach the lens cone and the cap to each other in the supplied configuration, and wherein the first snap features and the second snap features are configured to disengage from each other in response to a separation force to separate the lens cone and the cap.

2. The patient interface device assembly of claim 1, wherein an upper portion of the frustoconical shaped shell having largest diameters is exposed outside of the cap and a lower portion of the shell is disposed inside the cap.

3. The patient interface device assembly of claim 1, wherein the cap further includes an upper portion having a cylindrical shape with an outer diameter smaller than an outer diameter of the lower portion.

4. The patient interface device assembly of claim 1,
    wherein the cap further includes a circular step feature in its interior,
    wherein the lens cone further includes a circular step feature located at a smaller end of the frustoconical shaped shell, and
    wherein in the supplied configuration, the step feature of the lens cone rests on the step feature of the cap.

5. The patient interface device assembly of claim 4,
    wherein the cap further includes a plurality of slanted longitudinal ribs in its interior extending inwardly from an inner wall of the cap,
    wherein the frustoconical shaped shell of the lens cone further includes a corresponding plurality of longitudinally extending grooves along its outer surface, and
    wherein in the supplied configuration, the slanted longitudinal ribs of the cap fit in the longitudinally grooves of the shell.

6. The patient interface device assembly of claim 1, wherein the plurality of first snap features are a plurality of slots on the shell, and the plurality of second snap features are a plurality of protrusions that extend inwardly from an inner wall of the cap.

7. The patient interface device assembly of claim 1, wherein the shell of the lens cone further includes a plurality of bayonet mount slots located near a top edge of the shell and exposed above a top edge of the cap when the lens cone and the cap are in the supplied configuration, wherein the plurality of bayonet mount slots are configured to mate with a corresponding plurality of protruding pins on the ophthalmic surgical laser system.

8. A method of manually using the patient interface device assembly of claim 7 to couple the patient's eye to the ophthalmic surgical laser system, comprising:
    receiving the lens cone and the cap in the delivery configuration, wherein the lens cone is partially embedded inside the cap;

installing the lens cone on the ophthalmic laser system, including:
- holding the cap with the lens cone embedded therein, inserting the plurality of protruding pins of the ophthalmic surgical laser system into the plurality of bayonet mount slots of the lens cone, and twisting the cap to slide the bayonet mount slots relative to the pins, thereby attaching the lens cone to the ophthalmic surgical laser system; and
- pulling the cap to unsnap the cap from the lens cone;

coupling the suction ring to the patient's eye via the flexible skirt; and joining the lens cone and the suction ring to each other by inserting the portion of the lens cone into the receiving opening of the suction ring.

* * * * *